United States Patent [19]

Markwell et al.

[11] Patent Number: 5,010,097

[45] Date of Patent: Apr. 23, 1991

[54] NOVEL COMPOUNDS

[75] Inventors: Roger E. Markwell; Stephen A. Smith; Ian Hughes; Laramie M. Gaster, all of Harlow, England

[73] Assignee: Beecham Pharmaceuticals, Harlow, England

[21] Appl. No.: 287,453

[22] Filed: Dec. 20, 1988

[30] Foreign Application Priority Data

Dec. 22, 1987 [GB] United Kingdom ............. 8729804

[51] Int. Cl.⁵ ................. A61K 31/16; A61K 31/165; C07C 323/41
[52] U.S. Cl. ................................ 514/419; 514/315; 514/357; 514/423; 514/427; 514/438; 514/471; 514/513; 514/542; 514/550; 514/562; 514/616; 546/247; 546/336; 548/495; 548/540; 548/561; 549/79; 549/496; 558/256; 560/16; 560/147; 560/153; 562/426; 562/556; 564/154
[58] Field of Search ................ 564/154; 558/256; 562/426, 556; 560/16, 147, 153; 548/495; 514/419, 513, 542, 550, 562, 616

[56] References Cited

U.S. PATENT DOCUMENTS

| | | | |
|---|---|---|---|
| 4,256,761 | 3/1981 | Suh et al. | 564/154 X |
| 4,595,700 | 6/1986 | Donald et al. | 564/154 X |
| 4,681,966 | 7/1987 | Donald et al. | 564/154 X |

Primary Examiner—Richard L. Raymond
Attorney, Agent, or Firm—Hopgood, Calimafde, Kalil, Blaustein & Judlowe

[57] ABSTRACT

Novel compounds of the formula (I), a process for their preparation and their use as collagenase inhibitors are described:

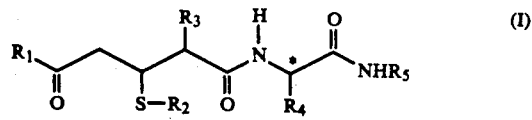

in which,
$R_1$ is hydrogen, alkyl, or optionally substituted aryl;
$R_2$ is hydrogen, or acyl such as

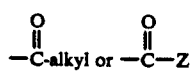

where Z is optionally substituted aryl;
$R_3$ is $C_{3-6}$ alkyl;
$R_4$ is hydrogen, alkyl, —CH₂—$R_{10}$ where $R_{10}$ is optionally substituted phenyl or heteroaryl, or a group

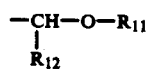

where $R_{11}$ is hydrogen, alkyl, or —CH₂—Ph where Ph is optionally substituted phenyl, and $R_{12}$ is hydrogen or alkyl; and
$R_5$ is hydrogen, alkyl, or a group

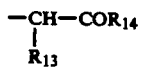

where $R_{13}$ is hydrogen, or alkyl, and $R_{14}$ is hydroxy, alkoxy, or —NR₆R₇, where each of $R_6$ and $R_7$ is hydrogen or alkyl, or $R_6$ and $R_7$ together with the nitrogen atom to which they are bonded form a 5-, 6- or 7-membered ring with an optional oxygen or sulphur atom in the ring or an optional further nitrogen atom optionally substituted by alkyl.

12 Claims, No Drawings

NOVEL COMPOUNDS

The present invention relates to novel thiol-ketone and thiol-aldehyde derivatives, processes for their preparation and their use in medicine. In particular, the present invention relates to their use as collagenase inhibitors for treating arthritic and other diseases.

The range of therapeutic applications of the collagenase inhibitors described hereinafter reflects the fundamental role of collagen within the connective tissue matrix throughout the body, and extends to many diseases not primarily due to collagen destruction but involving tissue remodelling, as these will also be susceptible to clinical intervention with collagenase inhibitors. In particular, inhibition of collagenases released from synovial and skin fibroblasts, chondrocytes, peripheral mononuclear cells, keratinocytes and gingival tissue, as well as inhibition of collagenase stored in polymorphonuclear leucocytes (PMNLs) should be of therapeutic value, and the present compounds are envisaged as having application against these and related mammalian collagenases.

Specifically, collagenase inhibitors will provide useful treatments for arthritic diseases such as rheumatoid arthritis and osteoarthritis, soft tissue rheumatism, polychondritis and tendonitis; for bone resorption diseases such as osteoporosis, Paget's disease, hyperparathyroidism and cholesteatoma; for the recessive classes of dystrophic epidermolysis bullosa; for periodontal disease and related consequences of gingival collagenase production or of PMNL collagenase production following cellular infiltration to inflamed gingiva; for corneal ulceration e.g. that induced by alkali or other burns, by radiation, by vitamin E deficiency or retinoid deficiency; and for systemic chemotherapy of cancer, where collagenase has been implicated in the neovascularization required to support tumour survival and growth, and in the penetration of tumour cells through the basement membrane of the vascular walls during metastasis. A collagenase inhibitor may also be of use in some post-operative conditions such as colonic anastomosis in which collagenase levels are raised.

As a particular example of the therapeutic value of collagenase inhibitors, chronic arthritic diseases lead to extensive loss of the collagen and proteoglycan components within the cartilage and bone of the affected joints. Neutral metalloproteases, especially collagenases and proteoglycanases, are currently thought to be the major enzymes involved.

These enzymes have been detected in extracts of synovial and cartilage tissue, and have also been extensively studied in tissue cultures of these organs. Apart from control of the biosynthesis or secretion of the enzymes, the most significant natural regulation of the activity of collagenase and proteoglycanase in the normal and diseased state, is considered to be the production of inhibitors such as the Tissue Inhibitor of Metalloproteases (TIMP) and $\alpha_2$-macroglobulin. An imbalance between the levels of proteolytic enzymes and natural inhibitors will allow destruction of the connective tissue components to proceed.

Restoration of the enzyme-inhibitor balance by treatment with synthetic inhibitors of collagenase thus offers a useful therapy for a wide range of connective tissue diseases in which collagenolytic activity is a causative or major contributory factor.

U.S. Pat. No. 4,595,700 discloses compounds of the formula (A):

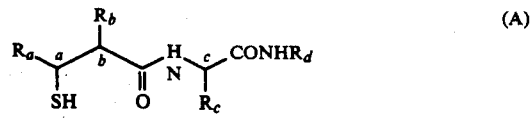

in which:

$R_a$ represents lower alkyl, phenyl or phenyl lower alkyl;

$R_b$ and $R_d$ represent lower alkyl; and $R_c$ represents lower alkyl, benzyloxyalkyl, alkoxybenzyl or benzyloxybenzyl wherein the oxyalkyl or alkoxy moiety contains 1 to 6 carbon atoms and a, b and c represent chiral centres with optional R or S stereochemistry.

These compounds are described as inhibitors of collagenase, useful in the treatment of rheumatoid arthritis and related diseases in which collagenolytic activity is a contributing factor.

A novel class of thiol-ketone and thiol-aldehyde derivatives has now been discovered, which are collagenase inhibitors and thus of potential utility in the treatment of diseases in which collagenolytic activity and tissue remodelling is implicated.

According to the present invention there is provided a compound of general formula (I), or a salt, solvate or hydrate thereof:

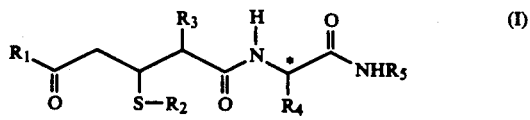

in which:

$R_1$ is hydrogen, alkyl, or optionally substituted aryl;

$R_2$ is hydrogen, or acyl such as

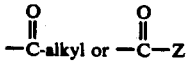

where Z is optionally substituted aryl;

$R_3$ is $C_{3-6}$ alkyl;

$R_4$ is hydrogen, alkyl, -CH$_2$-R$_{10}$ where R$_{10}$ is optionally substituted phenyl or heteroaryl, or a group

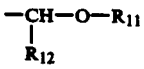

where $R_{11}$ is hydrogen, alkyl, or -CH$_2$-Ph where Ph is optionally substituted phenyl, and $R_{12}$ is hydrogen or alkyl; and $R_5$ is hydrogen, alkyl, or a group

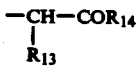

where $R_{13}$ is hydrogen, or alkyl, and $R_{14}$ is hydroxy, alkoxy, or $-NR_6R_7$, where each of $R_6$ and $R_7$ is hydrogen or alkyl, or $R_6$ and $R_7$ together with the nitrogen atom to which they are bonded form a 5-, 6- or 7-membered ring with an optional oxygen or sulphur atom in the ring or an optional further nitrogen atom optionally substituted by alkyl.

Unless otherwise specified, each alkyl or alkoxy group is a $C_{1-8}$ group, more preferably $C_{1-6}$, and may be a straight chain or branched. When used herein, the term aryl includes carbocyclic groups such as phenyl and naphthyl, preferably phenyl.

Optional substituents for aryl, phenyl and heteroaryl groups may be selected from OH, $C_{1-6}$ alkyl, $C_{1-6}$ alkoxy and halogen.

$R_1$ is preferably $C_{1-4}$ alkyl, especially methyl;
When $R_2$ is

Z is preferably an optionally substituted phenyl group. $R_1$ is preferably hydrogen,

or benzoyl.

$R_3$ is preferably a $C_4$ alkyl group, such as n-butyl, iso-butyl or sec-butyl, especially iso-butyl.

When $R_4$ is $-CH_2-R_{10}$ and $R_{10}$ is heteroaryl, values for $R_{10}$ include 5- or 6- membered monocyclic and 9- or 10membered bicyclic heteroaryl of which 9- or 10membered bicyclic heteroaryl is preferred.

In addition, 5- or 6- membered monocyclic and 9- or 10membered bicyclic heteroaryl preferably contain one or two heteroatoms selected from nitrogen, oxygen and sulphur which in the case of there being more than one heteroatom may be the same or different. When $R_{10}$ is 9- or 10- membered bicyclic heteroaryl the two rings are preferably fused with one 5- or 6- membered ring containing a single heteroatom.

Values for $R_4$ include iso-butyl, benzyl, or $C_{1-6}$ alkoxybenzyl such as 4-methoxybenzyl, 1-(benzyloxy)ethyl, or 9- or 10- membered fused bicyclic heteroarylmethyl such as 3-indolylmethyl. Preferably $R_4$ is 4-methoxybenzyl.

Values for R5 include hydrogen, alkyl such as methyl or ethyl, and 1-(methoxycarbonyl)ethyl. Preferably R5 is methyl.

The compounds of formula (I) may form salts with bases e.g. sodium hydroxide. When a basic nitrogen atom is present, the compounds of formula (I) may form acid addition salts e.g. with hydrochloric acid. Such compounds form part of the present invention.

Where compounds of formula (I), or salts thereof, form solvates such as hydrates, these also form an aspect of the invention.

The compounds of formula (I) have at least one asymmetric centre and therefore exist in more than one stereoisomeric form. The invention extends to all such forms and to mixtures thereof, including racemates, and diastereoisomeric mixtures.

Preferred isomers are those having the S configuration at the chiral centre marked with an asterisk in formula (I).

The compounds of formula (I) or their salts, solvates or hydrates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% by weight, preferably 75%, more preferably 90% and still more preferably 95% or 99% or more of the compound of formula I or its salt or solvate.

Compounds of formula (I) or their salts, solvates or hydrates may be isolated as crystalline solids or in the form of foams or gums.

One preferred pharmaceutically acceptable form is the crystalline form. The present invention provides the compounds of formula (I) or pharmaceutically acceptable salts or solvates thereof for use as active therapeutic agents, particularly as agents for treatment of musculo-skeletal disorders resulting from collagenolytic activity, particularly arthritic diseases, and tissue remodelling, and also for the systemic chemotherapy of cancer.

The present invention also provides a process for the preparation of a compound of formula (I) in which $R_2$ is hydrogen, which comprises cleaving a group L from a compound of formula (II):

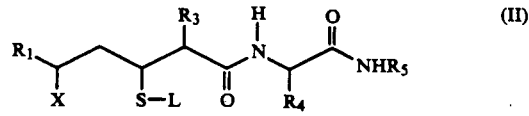

wherein L a conventional sulphur protecting group, X is a carbonyl group or a protected carbonyl group and $R_1$, $R_3$, $R_4$ and $R_5$ are as defined for formula (I), and when X is a protected carbonyl group, removing the protecting group.

Typically a protected carbonyl group is a ketal or acetal function, preferably a ketal function, for example 1,3-dioxolyl. Ketal and acetal functions may be removed under acid conditions, for example using hydrochloric acid in tetrahydrofuran.

Typically a protecting group L is a substituted benzyl group, such as alkoxybenzyl e.g. 4-methoxybenzyl or an aliphatic or aryl acyl group such as acetyl or benzoyl. When L is acyl it is of course identical to $R_2$, and so when X is a carbonyl group these compounds of formula (II) are themselves compounds of the invention.

When L is a substituted benzyl sulphur protecting group, such as 4-methoxy benzyl, then L may be removed by treatment with mercury acetate in trifluoroacetic acid containing anisole followed by reaction with hydrogen sulphide in dimethyl formamide, in a procedure analogous to that described in Chem. Pharm. Bull 1978, 26, 1576.

When L is an acyl group it may be removed by treatment with a base, for example aqueous ammonia or dilute aqueous sodium hydroxide, or by treatment with an acid, for example methanolic hydrochloric acid. Acid-labile carbonyl protecting groups such as ketals may be removed together with an L acyl group under acid conditions.

Other conventional methods for removing sulphur protecting groups may also be used.

Compounds of formula (II) may be prepared by treating a compound of formula (III):

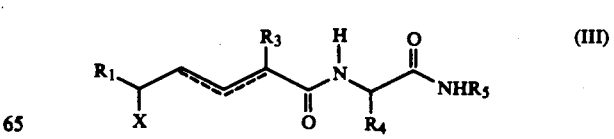

in which $R_1$, $R_3$, $R_4$, $R_5$ and X are as defined in formula (II) and the dotted line represents a double bond in a position either alpha or beta to variable $R_3$, with a thiol of formula (IV):

L-SH  (IV)

in which L is as defined in formula (II). When L is $R_2$ and X is a carbonyl group the compounds of formula (II) thereby produced are compounds of the invention.

Compounds of formula (II) in which L is an acyl group may also be prepared by treating a compound of formula V

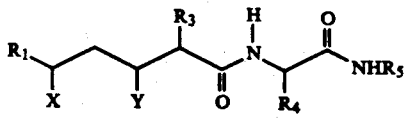

(V)

in which $R_1$, $R_3$, $R_4$, $R_5$ and X are as defined in formula (II) and Y is a labile leaving group, with a compound of formula (IV) or a sodium salt thereof:

L-SH  (IV)

in which L is an acyl group, according to the procedure of J. Houk and G. M. Whitesides, J. American Chem. Soc., 109, 6825, (1987).

Suitably Y is tosyloxy or trifluoromethanesulphonyloxy and L is acetyl.

Compounds of formula (V) as defined above may be prepared from compounds of formula (V) in which Y is hydroxy by reaction with a carboxylic acid-halide or anhydride in an inert solvent, for example p-toluenesulphonyl chloride or trifluoromethane-sulphonic anhydride in the presence of a base such as pyridine.

The intermediate compounds of formula (III) in which X is a protected carbonyl group and the double bond is in a position alpha to variable $R_3$ may be prepared by treating a compound of formula (VI):

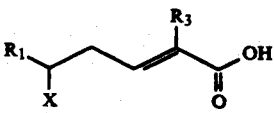

(VI)

in which X is a protected carbonyl group and $R_1$ and $R_3$ are as defined in formula (II), with a compound of formula (VII):

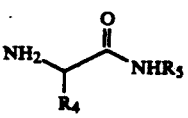

(VII)

in which $R_4$ and $R_5$ are as defined in formula (I).

The reaction is preferably carried out in the presence of a coupling agent such as 1,3-dicyclohexylcarbodiimide or 3-ethyl-1-(3-dimethylaminopropyl-carbodiimide.

Removal of the carbonyl protecting group under acid conditions provides a compound of formula (III) in which the double bond represented by the dotted line may be in a position either alpha or beta to variable R3.

The compounds of formula (IV) are known compounds.

The intermediate compounds of formula (V) in which X is a protected carbonyl group and Y is hydroxy may be prepared by treating a compound of formula (VIII):

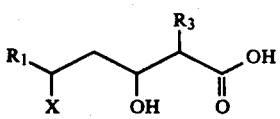

(VIII)

in which X is a protected carbonyl group and $R_1$ and $R_3$ are as defined in formula (I) with a compound of formula (VII) as defined above.

The compounds of formula (VII) are either known amino acid derivatives or can be made from these derivatives by known methods.

The intermediates of formulae (III), (V), (VI) and (VIII) disclosed herein are in some forms novel compounds and form an aspect of the present invention as do the described processes for their preparation.

Where obtainable, pharmaceutically acceptable salts of the compounds of formula (I) may be formed conventionally by reaction with the appropriate acid or base. Solvates may be formed by crystallization from the appropriate solvent.

As mentioned previously, the compounds of formula (I) exist in more than one diastereoisomeric form. Where the processes of the invention produce mixtures thereof, the individual isomers may be separated one from another by chromatography, e.g. HPLC.

Alternatively, separate diastereoisomeric compounds of formula (I) can be obtained by using stereoisomerically pure starting materials or by separating desired isomers of intermediates at any stage in the overall synthetic process, and converting these intermediates to compounds of formula (I).

The present invention further provides a pharmaceutical composition, which comprises a compound of formula (I), or a pharmaceutically acceptable salt, solvate or hydrate thereof, and a pharmaceutically acceptable carrier.

A composition of this invention is useful in the treatment of rheumatism and arthritis and in the treatment of other collagenolytic conditions.

A composition of the invention, which may be prepared by admixture, may contain a diluent, binder, filler, disintegrant, flavouring agent, colouring agent, lubricant or preservative in conventional manner. These conventional excipients may be employed in conventional manner, for example as in the preparation of compositions of related peptide enzyme inhibitors, such as the ACE inhibitor enalapril.

A composition of the invention may be adapted for oral, topical, percutaneous, rectal or parenteral-intravenous, intramuscular, sub-cutaneous, intradermal or intra-articular administration, but oral administration is preferred.

Preferably, a pharmaceutical composition of the invention is in unit dosage form and in a form adapted for use in the medical or veterinarial fields. For example, such preparations may be in a pack form accompanied by written or printed instructions for use as an agent in the treatment or prophylaxis of any of the disorders mentioned above.

The suitable dosage range for the compounds of the invention may vary from compound to compound and may depend on the condition to be treated. It will also depend, inter alia, upon the relation of potency to absorbability and the mode of administration chosen.

The compound or composition of the invention may be formulated for administration by any route, the preferred route depending upon the disorder for which treatment is required, and is preferably in unit dosage form or in a form that a human patient may administer to himself in a single dosage.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients. For example, in a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository or for parenteral administration in an injectable form. For injection, for example by intra-articular injection as poorly dispersed depot stores, the compounds of the invention may be presented in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, anti-oxidants or other preservatives, buffers or solutes to render the solution isotonic with the blood, thickening agents, suspending agents or other pharmaceutically acceptable additives. Such forms will be presented in sterile unit dose form such as ampoules or disposable injection devices or in multi- dose forms such as a bottle from which the appropriate dose may be withdrawn or a solid form or concentrate which can be used to prepare an injectable formulation.

For topical and percutaneous administration, the preparations may also be presented as an ointment, cream, lotion, gel, spray, aerosol, wash, skin paint or patch.

A unit dose for inflammatory diseases will generally contain from 10 to 1000 mg and preferably will contain from 10 to 500 mg, in particular 10, 50, 100, 150, 200, 250, 300, 350, 400, 450 or 500 mg. The composition may be administered once or more times a day, for example 2, 3 or 4 times daily, so that the total daily dose for a 70 kg adult will normally be in the range 10 to 3000 mg. Alternatively, in particular for injection, the unit dose will contain from 2 to 200 mg of a compound of the invention and be administered in multiples, if desired, to give the desired daily dose.

The present invention additionally provides a method of treating a collagenolytic condition such as rheumatism and/or arthritic conditions, or cancer, or other diseases in which enzyme-mediated breakdown of connective tissue components plays a role in mammals, such as humans, which comprises administering an effective amount of a compound of formula (I) or a pharmaceutically acceptable salt, solvate or hydrate thereof, to the mammal.

The present invention also provides the use of a compound of formula (I) or a pharmaceutically acceptable salt, solvate or hydrate thereof, for the manufacture of a medicament for use as an active therapeutic substance, particularly in the treatment of collagenolytic conditions, such as rheumatism, cancer, bone disorders, skin diseases, periodontal disease or corneal ulceration, in mammals.

The following Descriptions and Examples illustrate the preparation of compounds of the invention and the subsequent biological data illustrates their pharmacological activity. All temperatures are expressed in °C.

DESCRIPTION 1

α-(2-Methylpropyl)-2-methyl-1,3-dioxolane-2-but2'-enoic acid, methyl ester (D1)

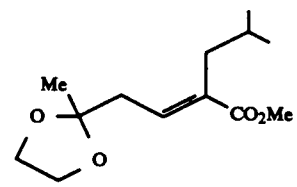

(D1)

2-(Diethylphosphono)-4-methylpentanoic acid methyl ester1 (5.0 g, 0.0188 mole) in dry toluene (22 ml) was treated at 20° C. with sodium hydride (0.614 g 80% suspension in oil, 0.0205 mole) under an atmosphere of nitrogen.

The mixture was heated under reflux for 40 min, cooled to room temperature and 2-methyl-1,3-dioxolane-2acetaldehyde-2 (2.72 g, 0.02 mole) in dry toluene (5 ml) was added over 10 min. After 16 h at room temperature, the mixture was partitioned between water and ether and the aqueous layer re-extracted further with ether.

The combined organic extracts were combined, washed with saturated sodium hydrogen carbonate solution, dried and evaporated in vacuo to give a colourless oil (3.0 g 66%).

δ (CDCl₃) 0.86 (6H, m); 1.30 (3H, s); 1.2-1.6 (1H, m); 2.1-2.2 (2H, m); 2.5 and 2.75 (2H, each d, J=8Hz); 3.65 (3H, s); 3.85 (4H, s); 5.76 and 6.72 (1H, each t, J=8 Hz).

REFERENCES

1. U.S. Pat. No. 4595700 (1986).
2. T. Ross Kelly et al., *Tetrahedron*, 40, 4569, (1984).

DESCRIPTION 2

α-(2-Methylpropyl)-2-methyl-1,3-dioxolane-2-but-2'-enoic acid (D2)

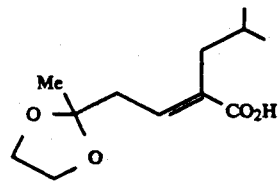

α-(2-Methylpropyl)-2-methyl-1,3-dioxolane-2-but-2'-enoic acid methyl ester (D1) (3.0 g, 0.0124 mol) was dissolved in ethanol (25 ml) and potassium hydroxide (1.38 g, 0.0246 mole) in water (20 ml) was added. The mixture was stirred under reflux for 16 h. The resulting solution was poured into water and citric acid solution was added until the solution reached pH 4. The product was extracted into ethylacetate and the combined organic extracts were dried and concentrated in vacuo to give a pale orange oil (2.47 g, 88%).

δ (CDCl₃) 0.88 (6H, m); 1.35 (3H, s); 1.4-1.8 (1H, m); 2.1-2.3 (H, m); 2.55 and 2.8 (2H, each d, J=7Hz); 3.9 (4H, s); 5.95 and 6.95 (1H, each t, J=7 Hz).

DESCRIPTION 3

N-(2-(4-methoxyophenyl)-1-S-(methylaminocarbonyl) ethyl-α-(2-methylpropyl)-2-methyl-1,3-dioxolane-2-but-2'-enamide (D3)

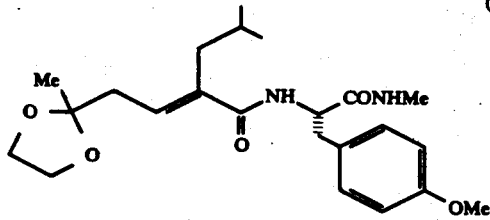

α-(2-Methylpropyl)-2-methyl-1,3-dioxolane-2-but-2'-enoic acid (D2) (2.39 g, 0.0105 mole) was dissolved in dry dichloromethane (30 ml) and the mixture was cooled to 0° C. 3-Ethyl-1-(3- dimethylaminopropyl)carbodiimide (2.02 g, 0.0105 mole) was added and the mixture was stirred for 10 min then O-methyl-L-tyrosine-N-methylamide (2.39 g, 0.0105 mole) in dry dichloromethane (15 ml) was added and the mixture was allowed to warm to room temperature and was stirred overnight. The organic mixture was washed with water twice, then dried and concentrated in vacuo to give a pale orange gum (3.54 g).

This was purified by column chromatography on silica gel using an increasing (to 5%) gradient of methanol in ethyl acetate to give 1.53 g (35%) of the title compound as a mixture of E and Z isomers.

δ (CDCl₃) 0.84 (6H, d, J=6 Hz); 1.32 (3H, s); 1.58 (1H, m); 2.18 (2H, d, J=7 Hz); 2.48 (2H, d, J=7 Hz);
2.73 (3H, d, J=5 Hz); 2.94-3.16 (2H, m); 3.79 (3H, s); 3.88-3.98 (4H, m); 4.58 (1H, q, J=6 Hz); 5.91 (1H, m); 6.22 (1H, t, J=7 Hz), 6.36 (1H, d, J=8 Hz); 6.82 (2H, d, J=8 Hz); 7.13 (2H, d, J=8 Hz).

Z isomer: & (CDCl₃) 0.71 (3H, d, J=7 Hz); 0.8 (3H, d, J=7 Hz); 1.33 (3H, s); 1.44 (1H, m); 1.95 and 2.26 (2H, each dd, J=7 Hz and 12 Hz); 2.42 and 2.55 (2H, each dd, J=7 Hz and 12 Hz); 2.75 (3H, d, J=5 Hz); 2.94-3.15 (2H, m); 3.79 (3H, s); 3.88-4.0 (4H, m); 4.64 (1H, q, J=7 Hz); 5.53 (1H, t, J=8 Hz); 6.24 (1H, m); 6.805 (2H, d, J=8 Hz); 7.13 (2H, d, J=8 Hz); 7.70 (1H, d, J=8 Hz).

DESCRIPTION 4

β-Acetylmercaoto-N-[2-(4-methoxvohenyl)-1-S-(methylaminocarbonyl)ethyl
-α-(2-methylpropyl)-2-methyl-1,3-dioxolane-2'-butanamide (D4)

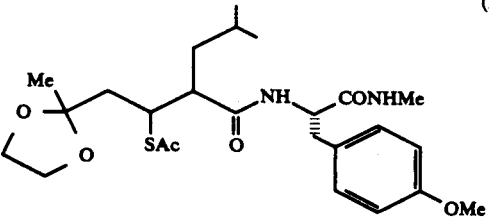

N-[2-(4-methoxyphenyl)-1-S-(methylaminocarbonyl)ethyl]-α-(2-methylpropyl)-2-methyl-1,3-dioxolane-2-but-2'-enamide (D3) (830 mg, 1.9 mmol) was dissolved in thiolacetic acid (20 ml) and the resulting solution was left to stand for 4 weeks. The excess thiolacetic acid was removed in vacuo and the residue purified by column chromatography on silica gel, eluting with ether, then ethyl acetate to give the desired product, as a mixture of isomers.

δ (CDCl₃) 0.9 (6H,m), 1.38 (3H,s), 2.43 (3H,m), 2.65 3 (1H,m), 2.85 (3H,d,J=5 Hz), 3.85 (m), 3.07
1 (1H,dd,J=7,14 Hz), 3.20 (1H,dd,J=6,14 Hz), 3.90 (3H,s),
3.8-4.15 (m), 4.3 (mm), 4.65 (1H,q,J=7 Hz), 5.63 (brs),
6 5.77 (brs), 6.23 (1H,d,J=7 Hz), 6.95 (2H,d,J=9 Hz) and
7.28 (2H,d,J=9 Hz).

DESCRIPTION 5

N-[2-(4-Methoxyphenyl)-1-S-(methylaminocarbonyl)ethyl]-2-(2-methylpropyl)-5-oxohex-2(and 3)-enamides (D5)

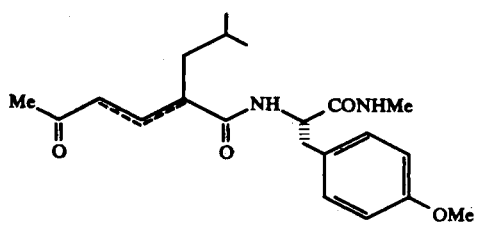

An ice-cooled solution of N-[2-(4-methoxyphenyl)-1-S(methylaminocarbonyl)ethyl]-α-(2-methylpropyl)-2methyl-1,3-dioxolane-2-but-2'-enamide (D3) (3.62g, 8.66 mmol) in tetrahydrofuran (40 ml) was treated with 18% hydrochloric acid (10 ml). After 16 h at room temperature, the solution was poured into saturated sodium hydrogen carbonate solution (200 ml) and was extracted with ethyl acetate. The extracts were washed with brine, dried (MgSO4) and evaporated in vacuo to leave the title compound (2.53 g, 78%) as a mixture of isomers, mp 60°-65° C.

EXAMPLE 1

3-Acetylmercapto-N-[2-(4-methoxyphenyl)-1-S-(methylaminocarbonyl)ethyl]2-(2-methylpropyl)-5-oxohexanamide (E1)

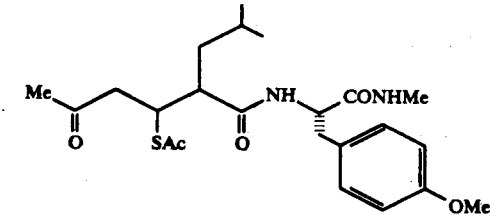

Method (a)

β-Acetylmercapto-N-[2-(4-methoxyphenyl)-1-S-(methylaminocarbonyl)ethyl]-α-(2-methylpropyl)-2-methyl-1,3-dioxolane-2'-butanamide (D4) is dissolved in tetrahydrofuran and 18% HCl is added. The reaction mixture is allowed to stand at room temperature overnight then the reaction mixture is poured into water and the product extracted into ethyl acetate. The ethyl acetate extracts are combined, dried and concentrated in vacuo to give the title compound.

More stringent reaction conditions (e.g. longer reaction time, increased temperature etc.) will also provide the compound described in Example 2 directly.

Method (b)

A solution of N-[2-(4-methoxyphenyl-1-S-(methylaminocarbonyl)ethyl]-2-(2-methylpropyl)-5-oxohex-2(and 3)-enamides (D5) (2.44 g, 6.5 mmol) in thiolacetic acid (90 ml) was kept at room temperature for 4 weeks, then the solvent was evaporated in vacuo. Column chromatography (250 g SiO2) of the residue, eluting first with ether, then with 50% ether/ethyl acetate gave two pairs of isomeric products.

Isomers A and B (approx 2:1)

δ (CDCl3): 0.85 (6H,t,J=7 Hz), 1.2-1.7 (3H,m), 2.05 (3H, 2 singlets), 2.30 (3H, 2 singlets), 2.60 (2H,d,J=6 Hz), 2.6-2.8 (1H,m), 2.73 (3h,d,J=5 Hz), 3.05 (2H,d,J=7 Hz), 3.77 (3H,s), 3.95 (1H,m), 4.55 (1H,q,J=7 Hz), 5.75 (1H,m), 6.35 (1/3H,d,J=8 Hz), 6.43 (2/3H,d,J=8 Hz), 6.83 (2H,d,J=8 Hz) and 7.16 (2H,d,J=8 Hz).

Isomers C and D (approx 2:1)

δ (CDCl3): 0.72 (3H,d,J=6 Hz), 0.78 (3H,d,J=6 Hz), 1.05-1.6 (3H,m), 2.13 (1/3H,s), 2.16 (2/3H,s), 2.30 (1H, 2 singlets), 2.5-2.9 (3H,m), 2.77 (3H,d,J=5 Hz), 3.0 (2H,m), 3.78 (3H,s), 4.05 (1H,m), 4.58 (1H,m), 6.0-6.2 (2H,m), 6.83 (2H,d,J=8 Hz) and 7.10 (2H,d,J=8 Hz).

EXAMPLE 2

3-Mercapto-N-[2-(4-methoxyphenyl)-1-S-(methylaminocarbonyl)ethyl]2-(2-methylpropyl)-5-oxohexanamide (E2)

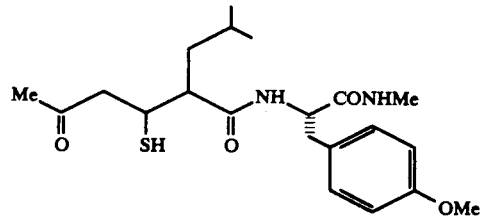

Each of the isomeric mixtures of 3-acetylmercapto-N-[2(4-methoxyphenyl)-1-S-(methylaminocarbonyl)ethyl]-2-(2-methylpropyl)-5-oxohexanamide (E1) were dissolved in nitrogen-purged methanol and the solution was cooled to 0° C. Aqueous ammonia (35%) was added and the mixture was stirred under nitrogen for 2 h. The solvent was removed in vacuo and the residue was triturated with 60°-80° petroleum ether. Column chromatography, eluting with ethyl acetate gave the title compound, isomers A/B and C/D.

The crude mixture of isomers A/B was triturated with ether to give a single isomer (E2A), as a white solid, m.p. 135°-138° C.

δ (CDCl3) 0.74 (3H,d,J=6 Hz), 0.80 (3H,d,J=6 Hz), 1 1-1.4 (2H,m), 2.03 (1H,d,J=9 Hz), 2.14 (3H,s), 2.42 (1H,m), 2.68 (1H,dd,J=7,15 Hz), 2.76 (3H,d,J=5 Hz), 2.87 (1H,dd,J=5,15 Hz), 2.99 (1H,dd,J=7,15 Hz), 3.10 (1H,dd,J=6,15 Hz), 3.32 (1H,m), 3.77 (3H,s), 4.67 (1H,q,J=7 Hz), 6.06 (1H,brd,J=8 Hz), 6.22 (1H,brs), 6.83 (2H,d,J=9 Hz) and 7.13 (2H,d,J=9 Hz).

Observed M+ 408.2085. $C_{21}H_{32}O_4N_2S$ requires M 408.2084.

The crude mixture of isomers C/D was triturated with ether to give a mixture of isomers (E2 C/D), as a white solid m.p. 160°-171° C.

Observed M+ 408.2081. $C_{21}H_{32}O_4N_2S$ requires M 408.2084.

COLLAGENASE INHIBITOR ASSAY

The test is performed essentially as in Cawston and Barrett Anal. Biochem. 99, 340-345 (1979). Compounds for testing are dissolved in methanol and added to purified human collagenase purified from culture supernatants from the human lung fibroblast cell line, WI-38, diluted in a suitable aqueous buffer. After a 5 min preincubation at 37° C., the assay tubes are cooled to 4° and $^{14}$C-acetylated rat skin Type I collagen is added. The assay tubes are incubated at 37° C. overnight. The $^{14}$C-collagen forms insoluble fibrils which are the substrate for the enzyme.

To terminate the assay, the assay tubes are spun at 12000 rpm for 25 min. Undigested $^{14}$C-collagen remains as insoluble fibrils and is pelleted, while digested $^{14}$C-collagen remains as soluble peptides in the supernatant. A sample of the supernatant is taken for liquid scintillation counting.

The activity of collagenase inhibitors (IC$_{50}$: 50% inhibitory concentration) is expressed as the concentration of compound that inhibits a known (standard) concentration of enzyme by 50%, or as the % inhibition of the collagen degradation caused by the known (standard) concentration of enzyme, at a stated concentration of the compound.

The activities of representative compounds of the invention are illustrated in the table below.

Inhibition of Human Lung Fibroblast Collagenase

| Example No. | Isomer | IC$_{50}$ (nm) |
| --- | --- | --- |
| 2 | A | 14 |
| 2 | C/D | 58% Inhibition at 1000 |

We claim:

1. A compound of formula (I) or a salt, solvate or hydrate thereof:

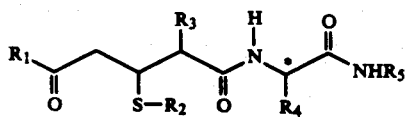

in which,

R$_1$ is hydrogen, alkyl, or optionally substituted aryl;
R$_2$ is hydrogen, or acyl;
R$_3$ is C$_{3-6}$ alkyl;
R$_4$ is hydrogen, alkyl, —CH$_2$-R$_{10}$ where R$_{10}$ is optionally substituted phenyl or heteroaryl, or a group

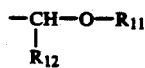

where

R$_1$ is hydrogen, alkyl, or —CH$_2$—Ph where Ph is optionally substituted phenyl, and R$_{12}$ is hydrogen or alkyl; and
R$_5$ is hydrogen, alkyl, or a group

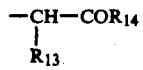

where

R$_{13}$ is hydrogen, or alkyl, and R$_{14}$ is hydroxy, alkoxy, or —NR$_6$R$_7$, where each of R$_6$ and R$_7$ is hydrogen or alkyl, or R$_6$ and R$_7$ together with the nitrogen atom to which they are bonded form a 5-, 6- or 7-membered ring with an optional oxygen or sulphur atom in the ring or an optional further nitrogen atom optionally substituted by alkyl.

2. A compound according to claim 1, in which R$_1$ is C$_{1-4}$ alkyl.

3. A COmpound according to claim 1, in which R$_2$ is hydrogen, or

4. A compound according to claim 1, in which R$_3$ is n-butyl, iso-butyl or sec-butyl.

5. A compound according to claim 1, in which R$_4$ is benzyl, 4-hydroxybenzyl, 4-methoxybenzyl or 3-indolylmethyl.

6. A compound according to claim 1, in which R$_5$ is hydrogen, C$_{1-4}$ alkyl or 1-(C$_{1-4}$ alkoxycarbonyl)ethyl.

7. A compound according to claim 1, in which R$_1$ is methyl; R$_2$ is hydrogen or acetyl; R$_3$ is iso-butyl; R$_4$ is 4-methoxybenzyl; and R$_5$ is methyl.

8. A compound according to claim 1, in which the chiral centre marked with an asterisk in formula (I) has the S-configuration.

9. A compound selected from 3-acetylmercapto-N-[2-(4-methoxyphenyl)-1-S-(methylaminocarbonyl)ethyl]-2-(2-methylpropyl)-5-oxo-hexanamide; and 3-mercapto-N-[2-(4-methoxyphenyl)-1-S-(methylaminocarbonyl)ethyl]-2-(2-methylpropyl)-5-oxo-hexanamide.

10. A pharmaceutically acceptable salt, solvate or hydrate of a compound according to claim 1.

11. A pharmaceutical composition comprising a compound of formula (I) as defined in claim 1, or a pharmaceutically acceptable salt, solvate or hydrate thereof, and a pharmaceutically acceptable carrier.

12. A method of treating collagenolytic conditions in mammals which comprises administering an effective amount of a compound of formula (I) as defined in claim 1, or a pharmaceutically acceptable salt, solvate or hydrate thereof to a sufferer.

* * * * *

UNITED STATES PATENT AND TRADEMARK OFFICE
CERTIFICATE OF CORRECTION

PATENT NO. : 5,010,097

DATED : April 23, 1991

INVENTOR(S) : Markwell et al.

It is certified that error appears in the above-identified patent and that said Letters Patent is hereby corrected as shown below:

Column 14, line 1, claim 1, the term $R_1$ should read -- $R_{11}$ --

Column 14, line 20, claim 3, the term COmpound should read -- compound --

Signed and Sealed this

Sixth Day of October, 1992

Attest:

DOUGLAS B. COMER

*Attesting Officer*     *Acting Commissioner of Patents and Trademarks*